US00PP29283P3

(12) United States Plant Patent
Smit

(10) Patent No.: US PP29,283 P3
(45) Date of Patent: May 8, 2018

(54) ***×GASTERALOE* PLANT NAMED 'AURORA'**

(50) Latin Name: ×*Gasteraloe* hybrid
Varietal Denomination: Aurora

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days. days.

(21) Appl. No.: 15/330,477

(22) Filed: Sep. 26, 2016

(65) Prior Publication Data

US 2018/0092279 P1 Mar. 29, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ... A01H 5/00; A01H 5/02; A01H 5/12; A01H 5/0244
See application file for complete search history.

(56) References Cited

PUBLICATIONS

Upov Pluto Plant Variety Database Sep. 23, 2017 for ×*Gasteraloe* 'Aurora' retrieved on Sep. 25, 2017, retrieved from the Internet at http://www.upov.int/pluto/en/index.jsp, one page.*

* cited by examiner

*Primary Examiner* — June Hwu

(57) ABSTRACT

A new cultivar of ×*Gasteraloe* plant named 'Aurora' that is characterized by a basal rosette plant shape and green serrated leaves with white spots and white teeth.

1 Drawing Sheet

Botanical classification: ×*Gasteraloe* hybrid.
Variety denomination: 'Aurora'.

BACKGROUND OF THE INVENTION

The present invention relates to a new and distinct cultivar of ×*Gasteraloe* plant botanically known as ×*Gasteraloe* hybrid and hereinafter referred to by the cultivar name 'Aurora'.

'Aurora' originated from the crossing of the female or seed parent, Gasteria 'Royal Wolfgang' (U.S. Plant Pat. No. 25,667) with the male or pollen parent, an unnamed *Aloe aristata* cultivar. The crossing was conducted in 2010 in Sappemeer, Netherlands. The resulting seeds were subsequently planted and grown. The cultivar 'Aurora' was selected by the inventor in 2012 in a controlled environment as a single plant within the progeny of the stated cross in a cultivated area of Sappemeer, Netherlands.

Asexual reproduction of the new cultivar 'Aurora' first occurred by leaf cuttings in 2012 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new ×*Gasteraloe* cultivar 'Aurora'. These traits in combination distinguish 'Aurora' as a new and distinct cultivar apart from other existing varieties of ×*Gasteraloe* known by the inventor.

1. ×*Gasteraloe* 'Aurora' exhibits green leaves with white spots.

2. ×*Gasteraloe* 'Aurora' exhibits leaf margins with white teeth.
3. ×*Gasteraloe* 'Aurora' exhibits a basal rosette plant shape.

The closest comparison cultivars are Aloe 'Tiki Zilla' (U.S. Plant Pat. No. 25,343) and plants of the species *Gasteraloe beguinii* (not patented). 'Aurora' is distinguishable from 'Tiki Zilla' by the following characteristics:

1. ×*Gasteraloe* 'Aurora' exhibits narrower leaves than the leaves of 'Tiki Zilla'.
2. ×*Gasteraloe* 'Aurora' exhibits lighter green colored leaves than the leaves of 'Tiki Zilla'.
3. ×*Gasteraloe* 'Aurora' exhibits a larger number of teeth on the leaf margins than the teeth on the leaf margins of 'Tiki Zilla'.

'Aurora' is distinguishable from plants of the species ×*Gasteraloe beguinii* by the following characteristics:

1. ×*Gasteraloe* 'Aurora' exhibits shorter and wider leaves than plants of the species *Gasteraloe beguinii.*
2. ×*Gasteraloe* 'Aurora' exhibits a less erect plant habit than plants of the species *Gasteraloe beguinii.*

'Aurora' is distinguishable from the female parent plant, by the following characteristics:

1. ×*Gasteraloe* 'Aurora' exhibits shorter leaves than the female parent plant.
2. ×*Gasteraloe* 'Aurora' exhibits a more compact habit than the female parent plant.

'Aurora' is distinguishable from the male parent plant by the following characteristics:

1. ×*Gasteraloe* 'Aurora' exhibits leaves that are wider and thicker than leaves of the male parent plant.
2. ×*Gasteraloe* 'Aurora' exhibits a more upright, erect growth habit. In comparison, the male parent plant exhibits a flatter growth habit.

BRIEF DESCRIPTION OF THE DRAWING

The accompanying photograph illustrates the distinguishing traits of ×*Gasteraloe* 'Aurora'. The photograph shows an overall view of a 24 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new ×*Gasteraloe* cultivar named 'Aurora'. Data was collected in Sappemeer, Netherlands from 24 month old plants grown in a glass greenhouse in 15 cm. diameter containers. The time of year was Winter and the temperature range was 18-20 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Aurora' has not been tested under all possible conditions and phenotypic differences may be observed with variations in environmental, climatic, and cultural conditions, however, without any variance in genotype.

Botanical classification: ×*Gasteraloe* hybrid 'Aurora'.

Annual or perennial: Perennial.

Parentage: 'Aurora' is a hybrid of the female parent, Gasteria 'Royal Wolfgang' and the male parent, an unknown *Aloe aristata* cultivar.

Plant type: Potted plant.

Growth habit: Basal rosette.

Plant shape: Globe shaped.

Suitable container size: 7 cm. pots or larger.

Plant height: 14.5 cm.

Plant width: 22.0 cm.

Vigor: Moderate.

Low temperature tolerance: 10° Centigrade.

High temperature tolerance: 35° Centigrade.

Propagation: Leaf cuttings and micro-propagation.

Time to initiate roots (summer): 14 days at 20° C.

Time to initiate roots (winter): 21 days at 20° C.

Time to produce a rooted cutting (summer): 80 days at 20° C.

Time to produce a rooted cutting (winter): 90 days at 20° C.

Growth rate: Moderate.

Crop time: Approximately 35 to 40 weeks in Sappemeer, Netherlands.

Root system: Fine and fibrous.

Plant fragrance: None.

Branching habit: Leaves arise in basal rosette, no branches.

Foliage:

*Leaf arrangement*.—Basal rosette.

*Compound or single*.—Single.

*Quantity of leaves per plant*.—Average 80.

*Leaf shape*.—Ovate to broad lanceolate, succulent.

*Leaf aspect*.—Concave.

*Leaf apex*.—Long apiculate.

*Leaf base*.—Broad cuneate.

*Leaf dimensions*.—11.0 cm. in length, 4.3 cm. in width and 1.0 cm. in thickness.

*Texture* (*both surfaces*).—Pustulate, covered with small dots, 0.2 cm. in diameter.

*Leaf luster*.—Matte (both surfaces).

*Leaf rugose*.—Not rugose.

*Pubescence*.—Absent.

*Leaf margin*.—Sharp serrate, teeth 0.1 cm. in length.

*Venation pattern*.—None visible.

*Young leaf color* (*upper surface*).—NN137B, towards base 144A to 144B, dots 193C, margin teeth NN155B.

*Young leaf color* (*lower surface*).—NN137B, towards base 144A to 144B, dots 193D, margin teeth NN155B.

*Mature leaf color* (*upper surface*).—Between 147A and N189A, towards base 194A to 194D, base 193D, dots 193C, margin teeth NN155B.

*Mature leaf color* (*lower surface*).—Between NN137A and 147A, towards base 137C, base 193D, dots 193D, margin teeth NN155B.

Flower: 'Aurora' has not produced flowers to date.

Fruit and seed: 'Aurora' has not produced fruit or seed to date.

Disease and pest resistance: Disease and pest resistance has not been observed.

I claim:

1. A new and distinct variety of ×*Gasteraloe* plant named 'Aurora' as described and illustrated.

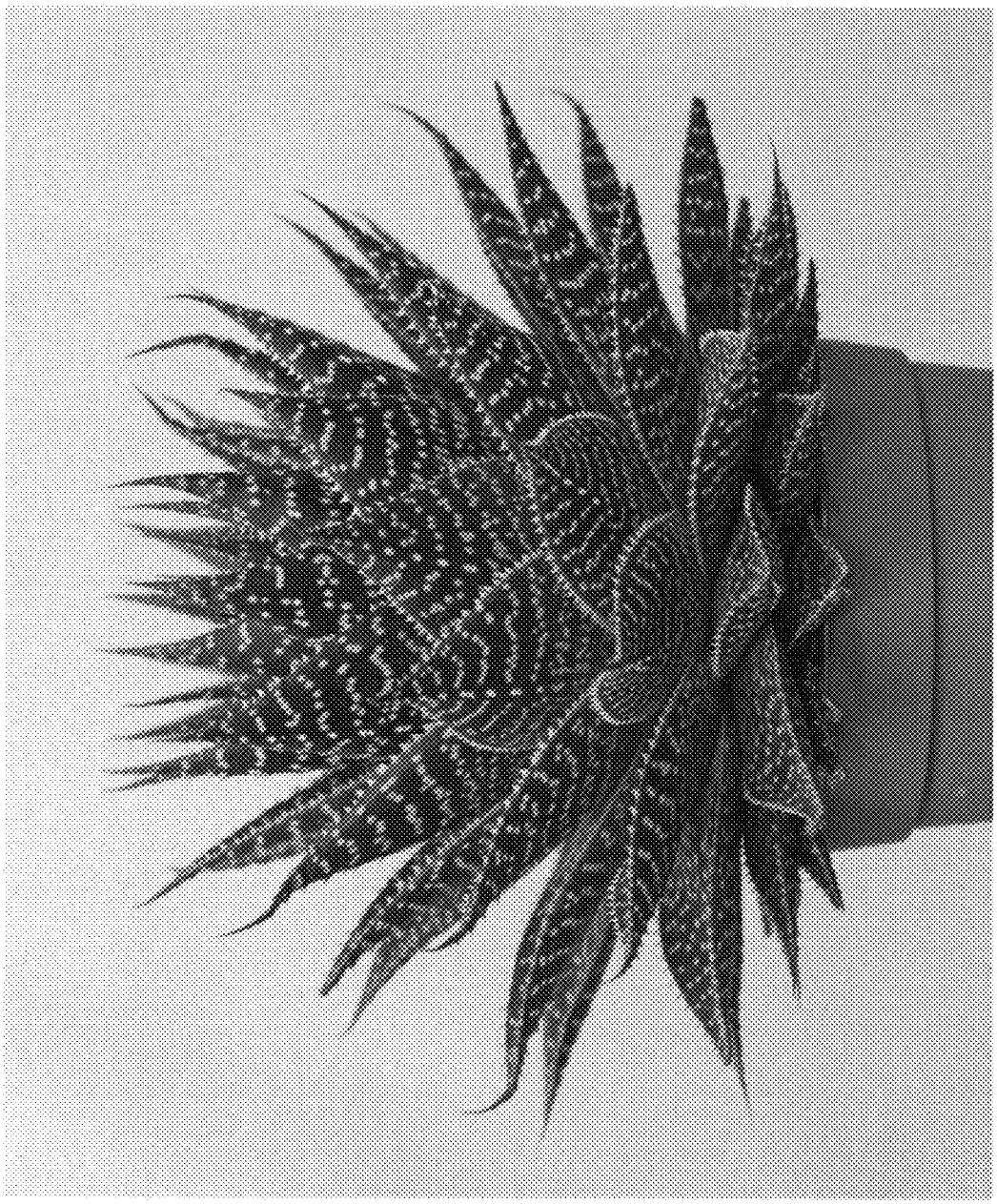

* * * * *